United States Patent [19]

Taheri

[11] Patent Number: 5,269,758
[45] Date of Patent: Dec. 14, 1993

[54] INTRAVASCULAR CATHETER AND METHOD FOR TREATMENT OF HYPOTHERMIA

[76] Inventor: Syde A. Taheri, 252 Dan Troy, Williamsville, N.Y. 14221

[21] Appl. No.: 875,683

[22] Filed: Apr. 29, 1992

[51] Int. Cl.$^5$ .................................... A61M 29/00
[52] U.S. Cl. ........................ 604/96; 606/27; 606/194; 607/106
[58] Field of Search .............. 604/96, 97, 113, 53; 606/27, 192, 194; 128/399–401

[56] References Cited

U.S. PATENT DOCUMENTS

| | | | |
|---|---|---|---|
| 1,652,954 | 12/1927 | Pierce | 606/192 |
| 2,024,301 | 12/1935 | Norwood | 606/192 |
| 4,646,719 | 3/1987 | Newar et al. | 606/192 |
| 4,754,752 | 7/1988 | Ginsburg et al. | 606/27 |
| 4,955,377 | 9/1990 | Lennox et al. | 606/27 |

FOREIGN PATENT DOCUMENTS 9105528  5/1991  PCT Int'l Appl. ................. 128/401

Primary Examiner—John D. Yasko
Assistant Examiner—Anthony Gutowski
Attorney, Agent, or Firm—Sommer, Oliverio & Sommer

[57] ABSTRACT

An improved intravascular device (20) is adapted for use in treating hypothermia in a patient. The improved device includes an elongated flexible catheter (21) having a distal end piece (26) arranged in spaced relation to a catheter main body portion (32). The distal end piece and catheter main body portions are joined by a wire stylet (33) and by a flexible wall portion (43). The stylet is adapted to be rotated relative to the catheter main body portion to selectively furl and unfurl the flexible wall portion. Once inserted into a patient blood vessel, a pump (25) is arranged to circulate heated fluid (e.g., heated saline solution) through communicating chambers (45,44) in heat exchange relation to blood flowing past the catheter. The pressure of fluid supplied by pump 25 may be caused to pulsate to prevent blood from clotting on the catheter.

12 Claims, 2 Drawing Sheets

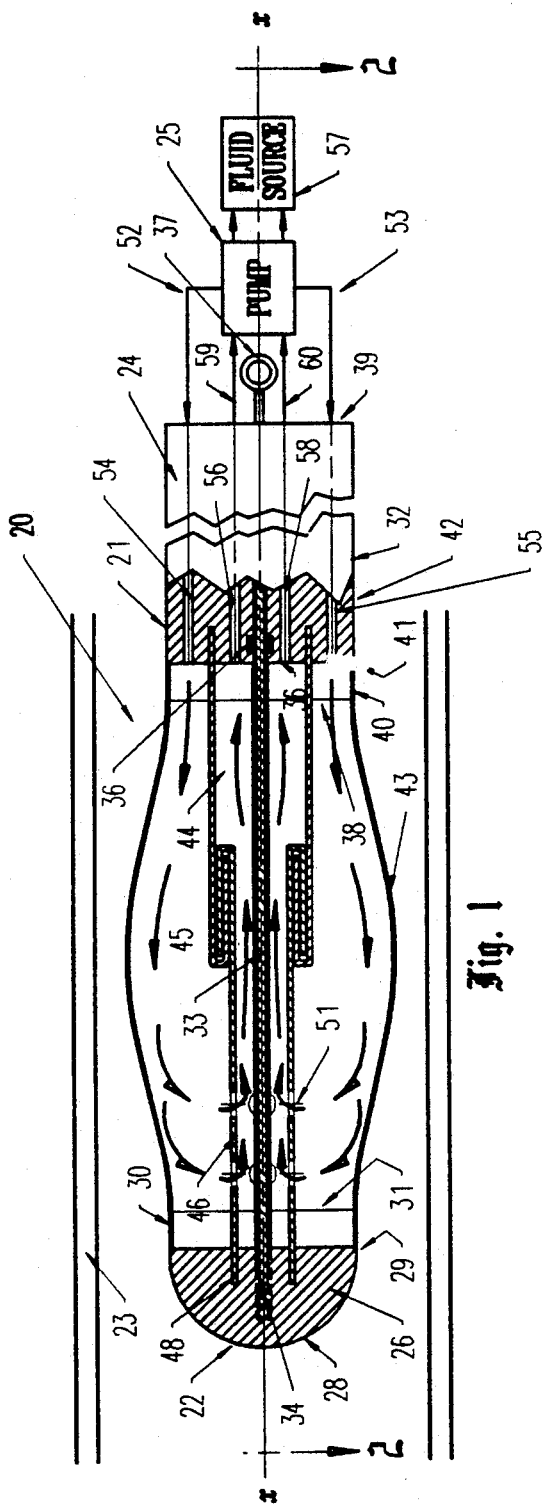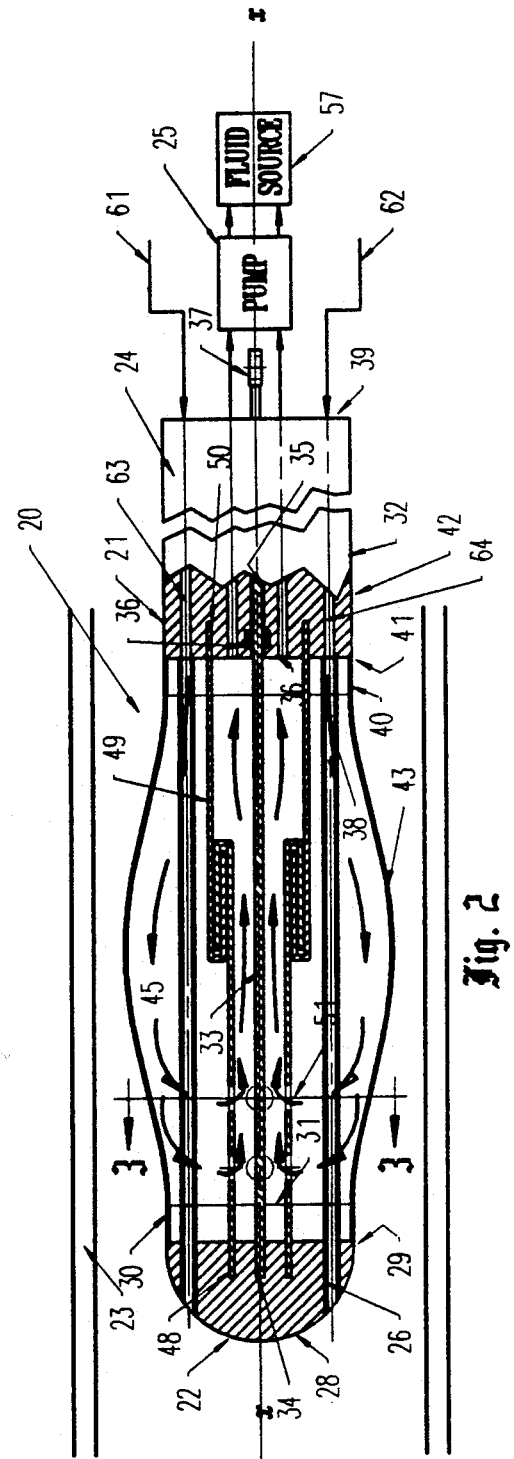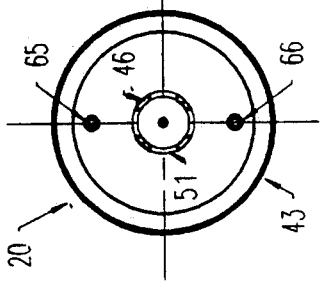

INTRAVASCULAR CATHETER AND METHOD FOR TREATMENT OF HYPOTHERMIA

TECHNICAL FIELD

This invention relates generally to the field of medical devices and instruments, and, more particularly, to an improved intravascular catheter for in-core treatment of hypothermia, with the option of simultaneously infusing fluid (e.g., blood, medication, etc.) into the patient's blood stream, and to a method of operating such a catheter.

BACKGROUND ART

Hypothermia is generally regarded as a lowering of the body temperature. If left unchecked, extreme hypothermia can lead to death. In treating hypothermia, the conventional technique is to warm the body topically. In some cases, however, this technique is not adequate. In other cases, the patient's blood is warmed by an extracorporeal heat exchanger.

Accordingly, there is believed to be a need for an improved device for, and technique for, treating hypothermia, either apart from or in conjunction with conventional topical warming techniques. At the same time, it would be generally desirable to have the additional capability of being able to infuse fluid, such as blood, medication, or the like, directly into the patient's blood stream while treating the patient for hypothermia.

DISCLOSURE OF THE INVENTION

With parenthetical reference to the preferred embodiment shown in the drawings, merely for purposes of illustration and not by way of limitation, the present invention broadly provides an improved intravascular device (20) for use in treating hypothermia in a patient. The improved device broadly includes an elongated flexible catheter (21) having a distal end (22) adapted to be inserted into the blood vessel (23) of a patient and moved therealong to a desired location within the patient's body, and having a proximal end (39) arranged to remain outside the patient's body, the catheter having an inflatable portion (43) adjacent the distal end, the inflatable portion having an outer surface arranged to contact blood flowing within the vessel and having an inner surface facing into a chamber (45), the inflatable portion being adapted to be moved between a deflated position (i.e., as shown in FIG. 4) in which the inner surface is arranged relatively close to the longitudinal axis (x—x) of the catheter and an inflated position (i.e., as shown in FIGS. 1 and 2) in which the inner surface is arranged relatively far from the longitudinal axis; and inflation means (25) positioned adjacent the proximal end and communicating with the chamber for selectively causing the inflatable portion to be moved between its deflated and inflated positions, and for causing a heated fluid to flow through the chamber in heat exchange relation to blood flowing past the catheter inflatable portion; whereby the distal end of the catheter may be inserted into a blood vessel and moved therealong to a desired position within the patient, and the inflation means may then be operated to cause the inflatable portion to move toward its inflatable position and to cause heated fluid to flow through the chamber to heat blood flowing past the inflatable portion.

In another aspect, the invention broadly provides an improved method of treating a patient suffering from hypothermia. This method broadly includes the steps of: making a suitable incision in a blood vessel; inserting the distal end (22) of an elongated flexible catheter (21) through the incision into the blood vessel; moving the catheter along the blood vessel to a desired location within the patient's body; inflating a chamber (45,44) within the catheter to cause an inflatable portion to move outwardly toward an inflated position; pulsing the pressure within the chamber to cause the flexible wall portion to oscillate in such inflated position; causing heated fluid to flow through said chamber in heat exchange relation to blood in the vessel; deflating the chamber to cause the flexible portion to move inwardly toward a deflated position; withdrawing the catheter from the blood vessel; and closing the incision.

Accordingly, the general object of the invention is to provide an improved catheter for use in treating hypothermia in a patient.

Another object is to provide an improved catheter which is adapted to be selectively inserted into a patient's blood vessel and which is adapted to provide in-core heating of a patient suffering from hypothermia.

Another object is to provide an improved catheter which is adapted for use in providing in-core heating of a patient suffering from hypothermia, with the option of simultaneously infusing a second fluid (e.g., blood, medication, etc.) into the patient's blood stream.

Another object is to provide an improved method of treating hypothermia in a patient.

These and other objects and advantages will become apparent from the foregoing and ongoing written specification, the drawings, and the appended claims.

BRIEF DESCRIPTION OF THE DRAWINGS

FIG. 1 is a fragmentary longitudinal view of the improved device, this view showing the distal marginal end portion in vertical section, showing the proximal marginal end portion in elevation, and showing the pump in schematic form.

FIG. 2 is a fragmentary horizontal sectional view thereof, taken generally on line 2—2 of FIG. 1.

FIG. 3 is a fragmentary transverse vertical section view thereof, taken generally on line 3—3 of FIG. 2.

DESCRIPTION OF THE PREFERRED EMBODIMENT(S)

Figure 4:
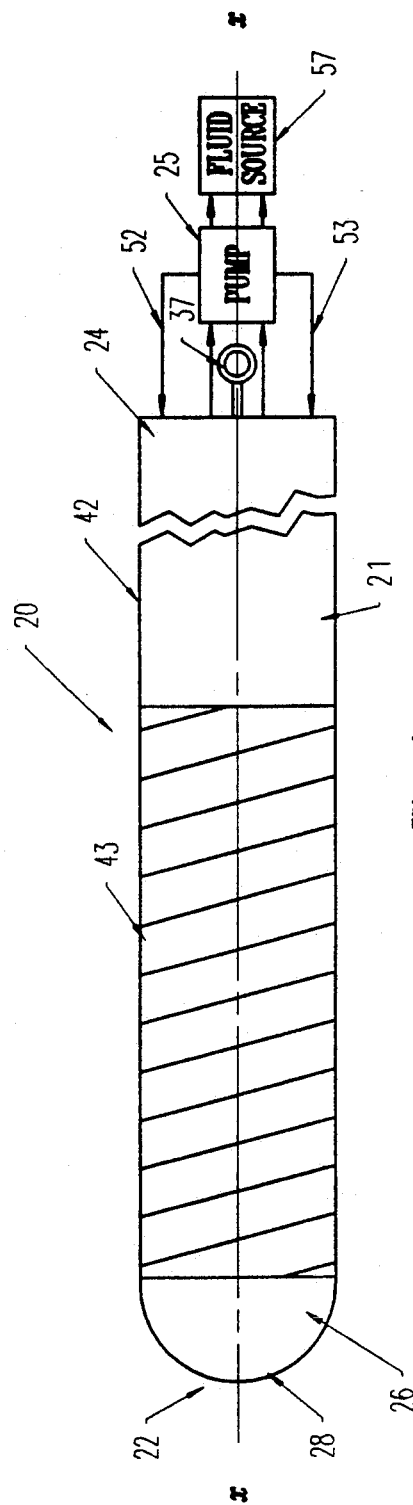
FIG. 4 is a side elevational view of the improved catheter, showing the flexible portion as having been furled to an out-of-the-way position.

At the outset, it should be clearly understood that like reference numerals are intended to identify the same structural elements, portions or surfaces consistently throughout the several drawing figures, as such elements, portions or surfaces may be further described or explained by the entire written specification of which this detailed description is an integral part. Unless otherwise indicated, the drawings are intended to be read (e.g., arrangement of parts, mounting, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.)

simply refer to the orientation of the illustrated structure as the particular drawing figure faces the reader. Unless otherwise indicated, the terms "inwardly" and "outwardly" refer to the orientation of a surface relative to its axis of elongation, or axis or rotation, as appropriate.

Turning now to the drawings, and, more particularly, to FIGS. 1-4 thereof, the improved intravascular device, generally indicated at 20 is shown as broadly including a horizontally-elongated flexible catheter, generally indicated at 21, having a leftward distal end 22 adapted to be inserted into the blood vessel 23 of a patient and moved therealong to a desired location within the patient's body, and having a proximal end 24 adapted to remain outside the patient's body. Inflation means, such as a pump 25, is arrange adjacent the proximal end for selectively causing an inflatable portion of the catheter to be moved between inflated and deflated positions, and for causing heated fluid, such as heated saline solution, to flow through a chamber within the inflatable portion in heat exchange relation to blood flowing through the vessel past the inflated portion.

The catheter is shown as being elongated along horizontal axis x—x, and has a leftward end piece 26 forming its distal end. End piece 26 is shown as being a horizontally-elongated specially-configured solid member 26 having a hemi-spherical left end face 28, a rightwardly-facing annular vertical surface 29 extending inwardly from the outer margin of surface 28, and an outwardly-facing horizontal cylindrical surface 30 continuing rightwardly therefrom and terminating in a circular vertical right end face 31.

End piece 26 is held in axially-spaced relation to the catheter main body 32 by means of a longitudinally extending stylet 33. The left marginal end portion of stylet 33 is fixedly received in an axial tapped blind hole 34 extending leftwardly into end piece 26 from its right end face 31, has an intermediate portion penetrating a central axial lumen 35 provided in catheter main body 32, and has a rightward ring 37 extending outwardly beyond the proximal end of the catheter. Ring 37 may be manually grasped and rotated relative to the catheter main body 32 to cause corresponding rotation of end piece 26 relative to the catheter main body. The space between stylet 33 and lumen 35 is sealed by means of an O-ring 36.

The catheter main body 32 is shown as having an annular vertical left end face 38, an annular vertical right end face 39. The outer surface of the catheter main body is shown as including, in pertinent part, a horizontal cylindrical surface 40 extending rightwardly from the outer margin of left end face 38, a leftwardly-facing annular vertical surface 41, and a horizontal cylindrical surface 42 continuing rightwardly therefrom to join the outer margin of right end face 39. Stylet 33 may be selectively rotated in the appropriate angular direction relative to the catheter main body 32. When this occurs, the distal end piece 26 will rotate with the stylet, to selectively furl or unfurl the flexible portion 43 about the disjointed device. The catheter distal end piece and main body are also joined by a flexible portion, generally indicated at 43, which somewhat resembles a tubular sleeve. This may be formed of a thin-walled tubular plastic material, or some other functionally-equivalent material. The left marginal end portion of inflatable portion 43 is shown as overlapping distal end piece surface 30, and may be secured in this position by means of a suitable adhesive. Similarly, the right marginal end portion of flexible portion 43 is shown as overlapping catheter main body surface 40, and may be similarly held in this position by means of a suitable adhesive.

A horizontally-elongated tubular partition 47 is shown as dividing the chamber within the flexible portion 43 into an inner chamber 44 and an outer chamber 45. Partition 47 consists of two members mounted for rotation relative to one another. The first member 46 is depicted as being a horizontally-elongated thin-walled tubular metal member having its left marginal end portion received in an annular groove 48 extending leftwardly into the distal end piece from its right end face 31. The right marginal end portion of partition first part 46 is reversely folded outwardly and back upon itself in spaced relation thereto. The partition right part 49 is depicted as having its right marginal end portion suitably received in an annular groove 50 extending rightwardly into the catheter main body portion from its left end face 38. The left marginal end portion of the catheter right body part is reversely folded inwardly and back upon itself in spaced relation thereto. Thus, the folded-back portions of the two partition parts fit interdigitally, as shown in FIGS. 1 and 2. This permits an operator to rotate the stylet and end piece relative to the main catheter body, while effectively maintaining the partition to separate the inner and outer chambers 44,45, respectively. The partition first part 46 is shown as having two sets of axially-spaced radial through-holes, severally indicated at 51. In each set, there are four openings arranged at 90 degree intervals, as shown in FIG. 3.

As best shown in FIG. 1, the pump 25 is arranged to supply heated fluid, such as heated saline solution, from a fluid source 57 via lines 52,53 and lumens 54, 55 to catheter outer chamber 45. Such fluid will then flow through outer chamber 45, through the several holes 51 to enter inner chamber 44, from which it is conveyed via lumens 56,58 and lines 59,60, respectively, back to the pump and source. Thus, the pump may be operated to circulate heated fluid through the outer and inner chambers, At the same time, the pump may be operated to pressurize said fluid so as to cause flexible portion 43 to bow outwardly to an inflated position (as shown in FIGS. 1 and 2), and may be further caused to pulsate the pressure of such fluid so as to cause flexible wall portion 43 to oscillate, thereby preventing blood from clotting on the flexible portion.

As best shown in FIG. 2, another fluid (e.g., blood, medication or the like) may be selectively infused into the blood vessel via lines 61,62, lumens 63,64 and conduits 65,66, respectively, having their left marginal end portions penetrating distal end piece 26. Thus, this additional fluid may be infused into the blood stream simultaneously with the provision and supply of heated fluid to chambers 44,45.

Figure 5:
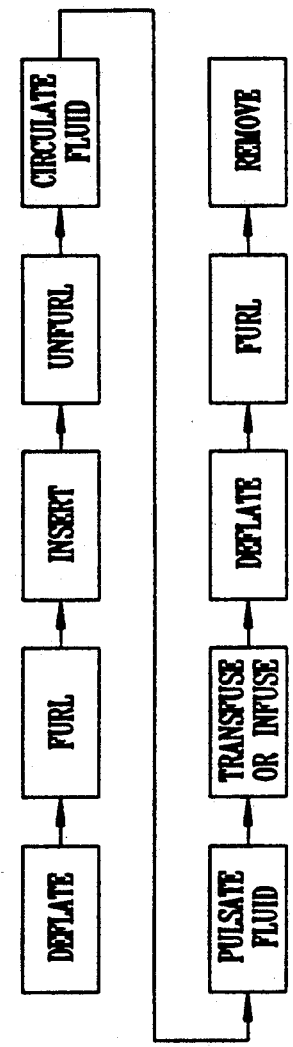
FIG. 5 is a block diagram showing the operational sequence of steps used in operating the improved catheter.

The sequence of operation is generally shown in FIG. 5. First, pump 25 is operated so as to deflate chambers 44,45. These may be deflated to atmospheric pressure, or to a negative pressure. The surgeon then grasps the free end 37 of stylet 33, and rotates it relative to the catheter main body, to selectively furl the flexible portion, as shown in FIG. 4. The surgeon then makes an incision in the appropriate blood vessel, and inserts the distal end of the deflated and furled catheter. The catheter is then moved longitudinally along the blood vessel until it is in a desired position within the patient's body. Once in this position, the surgeon rotates the stylet relative to the catheter main body portion, to unfurl the flexible portion. He then operates the pump so as to circulate heated fluid through outer chamber 45, holes 51, and inner chamber 44. The pressure supplied to these chambers will typically be above the patient's blood pressure, such that the flexible wall portion will bow outwardly, as shown in FIGS. 1 and 2. This tends to reduce the size of the annular opening between the inflated portion 43 and the blood vessel. The operator then causes such heated saline solution to circulate through the catheter in heat exchange relation to the blood flowing therepast. Blood flowing past the inflated portion through this constricted annular passageway is therefore warmed by the heated fluid circulating in chambers 45,44. As noted above, the pressure may be pulsated to prevent blood from clotting on the inflated catheter portion.

If desired, the surgeon may simultaneously infuse another fluid, such as blood or medication, through conduits 65,66 independently of the heating function provided by the pump.

Thereafter, pump 25 is operated so as deflate the chambers. The surgeon may grasp and rotate the proximal end 37 of stylet 33 to re-furl the deflated flexible wall portion about the catheter. Finally, the catheter is removed from the blood vessel via the incision through which it was inserted, and, the incision is thereafter closed.

Therefore, the invention provides an improved intravascular catheter which is adapted for use in treating a patient suffering from hypothermia, with the option of simultaneously infusing a second fluid into the patient's blood stream.

Modifications

The present invention contemplates that many changes and modifications may be made. For example, the shapes and materials of the various component parts may be readily changed as desired. Other types of partitions affording the capability of a rotational slippage, may be substituted for the partition shown. The provision of lumens 65,66 for infusing second fluid into the blood vessel during operation of the heat exchange function of the catheter, is optional, and may be omitted. In some cases, the steps of furling an unfurling the flexible wall portion may be omitted entirely. Various types of pumps and circulating mechanisms may be employed.

Therefore, while a preferred embodiment of the improved intravascular device has been shown and described, and several modifications thereof discussed, persons skilled in this art will readily appreciate that various additional changes and modifications may be made without departing from the spirit of the invention, as defined and differentiated by the following claims.

What is claimed is:

1. An intravascular device for use in treating hypothermia in a patient, comprising:

an elongated flexible catheter having a distal end adapted to be inserted into a blood vessel of said patient and moved therealong to a desired location within the patient's body, and having a proximal end adapted to remain outside the patient's body, said catheter having an inflatable portion adjacent said distal end, said inflatable portion having an outer surface arranged to contact blood within said vessel and having an inner surface facing into a chamber, said inflatable portion being adapted to be moved between a deflated position in which said inner surface is arranged relatively close to the longitudinal axis of said catheter and an inflated position in which said inner surface is arranged relatively far from said longitudinal axis, said catheter having an end piece converted to said inflatable portion at said distal said catheter end, having a main body spaced from said end piece by said inflatable portion and terminating in said proximal end, said end piece being arranged for movement relative to said main body, said main body having a first lumen converted to said inflatable portion and;

inflation means positioned proximate said proximal end and communicating with said chamber for selectively causing said inflatable portion to be moved between said deflated and inflated positions, and for causing a heated fluid to flow simultaneously into and out of said chamber in heat exchange relation to blood flowing past said catheter inflatable portion; and a stylet having a distal end secured to said end piece, having an intermediate portion movably arranged within said first lumen, and having a proximal end arranged adjacent the proximal end of said main body, and wherein said stylet may be selectively rotated relative to said main body to move said inflatable portion between furled and unfurled positions;

whereby the distal end of said catheter may be inserted into a blood vessel and moved therealong to a desired position within said patient, and said inflation means may be operated to cause said inflatable portion to move toward said inflated position and to cause heated fluid to flow through said chamber to heat blood flowing past said inflated portion.

2. An intravascular device as set forth in claim 1, and further comprising a wall within said chamber and extending between said end piece and said main body, said wall separating said chamber into inner and outer chambers, said wall having at least one opening communicating said inner and outer chambers, and wherein said main body has a second lumen communicating with said outer chamber and a third lumen communicating with said inner chamber.

3. An intravascular device as set forth in claim 2 wherein said inflation means is arranged to cause heated fluid to flow through said second lumen, said outer chamber, said opening, said inner chamber, and said third lumen.

4. An intravascular device as set forth in claim 3 wherein said heated fluid is a liquid.

5. An intravascular device as set forth in claim 3 wherein said inflation means is arranged to control the pressures of fluid in said inner and outer chambers so as to selectively cause said inflatable portion to move between said deflated and inflated positions.

6. An intravascular device as set forth in claim 5 wherein said inflation means is arranged to cause the pressure of fluid in said outer chamber to oscillate when said inflatable portion is in said inflated position.

7. An intravascular device as set forth in claim 2 wherein said catheter has a fourth lumen extending between said distal end and said proximal end for allowing fluid to be infused into said blood vessel.

8. An intravascular device as set forth in claim 1 wherein said inflatable portion is formed of plastic.

9. The method of treating a patient suffering from hypothermia, comprising the steps of:

making a suitable incision in a blood vessel;

inserting the distal end of an elongated flexible catheter through said incision into said blood vessel;

moving said catheter along said blood vessel to a desired location within the patient's body;

inflating a chamber within said catheter to cause an inflatable portion to move outwardly toward an inflated position;

pulsing the pressure within said chamber to cause said inflatable portion to oscillate in said inflated position;

causing heated fluid to flow through said chamber in heat exchange relation to blood in said vessel;

deflating said chamber to cause said inflatable portion to move inwardly toward a deflated position;

withdrawing said catheter from said blood vessel; and closing said incision;

thereby to transfer heat to the blood of said patient.

10. The method as set forth in claim 9 and further comprising the additional step of unfurling said inflatable portion when said catheter is in said desired location and before said chamber is inflated.

11. The method as set forth in claim 9 and further comprising the additional step of furling said inflatable portion after said chamber has been deflated and before said catheter is withdrawn.

12. The method as set forth in claim 9 and further comprising the additional step of infusing a fluid into said blood vessel through said catheter while said inflatable portion is in said inflated position.

* * * * *